(12) United States Patent
De Smit et al.

(10) Patent No.: US 10,508,063 B2
(45) Date of Patent: Dec. 17, 2019

(54) OLEFIN OLIGOMERIZATION IN THE PRESENCE OF CYCLOPENTENE

(71) Applicant: ExxonMobil Chemical Patents Inc., Baytown, TX (US)

(72) Inventors: Emiel De Smit, Brussels (BE); Mechilium J. G. Janssen, Leuven (BE); Marc P. H. Puttemans, Schepdaal (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/550,700

(22) PCT Filed: Nov. 27, 2015

(86) PCT No.: PCT/EP2015/077935
§ 371 (c)(1),
(2) Date: Aug. 11, 2017

(87) PCT Pub. No.: WO2016/150529
PCT Pub. Date: Sep. 29, 2016

(65) Prior Publication Data
US 2018/0037520 A1 Feb. 8, 2018

(30) Foreign Application Priority Data
Mar. 20, 2015 (EP) .................... 15159993

(51) Int. Cl.
*C07C 2/12* (2006.01)
*B01J 29/70* (2006.01)

(52) U.S. Cl.
CPC ............. *C07C 2/12* (2013.01); *B01J 29/7026* (2013.01); *C07C 2529/70* (2013.01)

(58) Field of Classification Search
None
See application file for complete search history.

(56) References Cited

U.S. PATENT DOCUMENTS

| 5,177,282 A | 1/1993 | Nierlich et al. |
| 2003/0171632 A1* | 9/2003 | Du Toit ................. C10G 50/00 585/533 |

(Continued)

FOREIGN PATENT DOCUMENTS

| EP | 2 072 484 A1 | 6/2009 |
| WO | 02/060842 A | 8/2002 |

OTHER PUBLICATIONS

Martens J.A. et al: "Tailored Alkene Oligomerization with H-ZSM-57 Zeolite", Angewandte Chemie International Edition, Wiley—VCH Verlag GmbH & Co. KGAA, DE, vol. 39, No. 23, Dec. 4, 2000, pp. 4376-4379.

(Continued)

*Primary Examiner* — Philip Y Louie
(74) *Attorney, Agent, or Firm* — Darryl M. Tyus

(57) ABSTRACT

Process for converting an olefin containing hydrocarbon feed into an oligomerization product or a hydrogenated oligomerization product, comprising contacting the feed in a reactor with an oligomerization catalyst under conditions suitable to oligomerize the olefin to obtain an oligomerization product and optionally hydrogenating the oligomerization product wherein the content of the at least one $C_4$-, $C_5$-, $C_6$- or $C_7$-cyclic olefin in the feed is controlled.

21 Claims, 4 Drawing Sheets

(56) References Cited

U.S. PATENT DOCUMENTS

2007/0255081 A1 11/2007 Beadle et al.
2012/0116141 A1 5/2012 Godsmark et al.

OTHER PUBLICATIONS

Laura Boggioni and Incoronata Tritto: "State of the Art of Cyclic Olefin Polymers", Materials Research Society, vol. 38. No. 03, 2013, pp. 245-251.

* cited by examiner

OLEFIN OLIGOMERIZATION IN THE PRESENCE OF CYCLOPENTENE

CROSS REFERENCE TO RELATED APPLICATIONS

This application is a National Phase Application of PCT Application Serial No. PCT/EP2015/077935 filed Nov. 27, 2015, and claims priority to and the benefits of European Application No. 15159993.3, filed Mar. 20, 2015, which are hereby incorporated by reference in their entireties.

The present invention relates to a process for converting an olefin containing hydrocarbon feed into an oligomerization product or a hydrogenated oligomerization product wherein the level of at least one cyclic olefin present in the feed is controlled such that it is at, below or above a predetermined level to obtain desired effects such as an extension of catalyst life and/or desired product characteristics.

BACKGROUND

The condensation reaction of an olefin or a mixture of olefins over an acid catalyst to form higher molecular weight products is a widely used commercial process. This type of condensation reaction is known as an oligomerization reaction, and the products are low molecular weight oligomers which are formed by the condensation of up to 12, typically 2, 3 or 4, but up to 5, 6, 7, or even 8 olefin molecules with each other. Specifically, low molecular weight olefins, such as propene, 2-methylpropene, 1-butene and 2-butenes, pentenes and hexenes, can be converted by oligomerization over a zeolite catalyst or another suitable catalyst to a product which is comprised of oligomers and which is of value as a high-octane gasoline blending stock and as a starting material for the production of chemical intermediates and end-products. Such chemical intermediates and end-products include alcohols, acids, detergents and esters such as plasticizer esters and synthetic lubricants. Industrial oligomerization reactions are generally performed in a plurality of tubular or chamber reactors. Sulphated zirconia catalysts, liquid or solid phosphoric acid catalysts and sulphuric acid catalysts are also known catalysts for oligomerization.

Industrial hydrocarbon conversion processes employing zeolite catalysts typically run for several weeks before a catalyst change is required or a decommissioning of the reactor is needed. In industrial processes, the feeds for the reactions are generally obtained from refining activities such as a stream derived from catalytic or steam cracking, which may have been subjected to fractionation. The nature of the refining activities is such that there will be variations in the composition of the feed. In addition it may be desired to change the nature of the feed during a reactor run. However, these variations and changes may influence the activity and life of the catalyst and/or properties of the resulting products. Furthermore, the oligomerization reactions are exothermic and the size of the exotherm also depends upon the nature and amount of olefin present in the feed. Isobutylene and propylene are particularly reactive generating a large amount of heat per unit of mass reacting. This in turn may influence the performance of the catalyst and the characteristics of the products formed in the reaction.

Thus, in the prior art concerned with processes for the oligomerization of olefins, numerous approaches have been developed with regard to ensuring acceptable catalyst life and activity and controlling desired product characteristics.

For example, US-A-2007/0255081 (WO2005/058777) describes a process for the conversion of olefins in a reactor which process comprises continuously passing a feed comprising an olefin and water through a bed of catalyst under conversion conditions to form a conversion product, the water content of the feed being automatically controlled according to an analysis of the composition of the feed. Thus, the process of US-A-2007/0255081 adjusts the content of water in the feed as a means to control and optimize the process.

US-A-2012/0116141 (WO 2007/006398) describes a process for oligomerizing an olefin comprising contacting the olefin with a zeolite catalyst in a reactor tube of a tubular reactor having a shell that contains a temperature control fluid for removing heat of reaction from the reactor tube, in which process the olefin feed to the reactor contains at least 42 wt % of olefin, wherein operating conditions are controlled such that the reaction product mixture exiting the reactor is at a pressure of at least 55 barg and wherein the shell side temperature control fluid parameters are controlled such that the peak temperature in the reactor tube is no more than 50° C. above the temperature of the temperature control fluid as said fluid exits the reactor. Thus, the process of US-A-2012/0116141 uses a specific reactor design and temperature profile to control and optimize the process, in particular with regard to catalyst life and conversion achieved.

However, in view of the variations in the feed materials as noted above, there remains a need for providing further processes for the oligomerization of an olefin comprising contacting an olefin feed with an oligomerization catalyst under conditions suitable to oligomerize the olefin, which processes provide for alternative or further means for controlling and/or improving said type of process, in particular with regard to catalyst life and/or the desired composition of the products to be obtained.

SUMMARY OF THE INVENTION

The present invention solves the above problem by adjusting the content of cyclic olefins, also called cycloalkenes, in particular cyclopentene, present in an olefin containing hydrocarbon feed so that said content is at, below or above a predetermined level which ensures that the desired catalyst life and/or a desired composition of the product is achieved.

Accordingly, the present invention relates to a process for converting an olefin containing hydrocarbon feed into an oligomerization product, said process comprising contacting the feed in a reactor with an oligomerization catalyst under conditions suitable to oligomerize the olefin to obtain an oligomerization product, said olefin feed material comprising at least one $C_2$ to $C_{12}$ acyclic olefin and at least one cyclic olefin in which the ring is $C_4$-, $C_5$-, $C_6$- or $C_7$-membered (also termed $C_4$-, $C_5$-, $C_6$- or $C_7$-cyclic olefin herein), wherein the content of at least one of the $C_4$-, $C_5$-, $C_6$- or $C_7$-cyclic olefin in the feed is controlled such that it is at, below or above a predetermined level. According to this invention the oligomerization product as obtained above may then be subject to hydrogenation. Accordingly, the present invention relates to a process for converting an olefin containing hydrocarbon feed into an oligomerization product or a hydrogenated oligomerization product, said process comprising contacting the feed in a reactor with an oligomerization catalyst under conditions suitable to oligomerize the olefin to obtain an oligomerization product and optionally hydrogenating the oligomerization product, said olefin feed material comprising at least one $C_2$ to $C_{12}$ acyclic olefin and at least one $C_4$-, $C_5$-, $C_6$- or $C_7$-cyclic olefin herein, wherein the content of at least one of the $C_4$-, $C_5$-, $C_6$- or $C_7$-cyclic olefin in the feed is controlled such that it is at, below or above a predetermined level.

According to a further aspect, the present invention relates to a process for extending (increasing) the life of an oligomerization catalyst used in a process for converting an olefin containing hydrocarbon feed into an oligomerization product or a hydrogenated oligomerization product, said process comprising contacting the feed in a reactor with the oligomerization catalyst under conditions suitable to oligomerize the olefin to obtain an oligomerization product and optionally hydrogenating the oligomerization product, said olefin feed material comprising at least one $C_2$ to $C_{12}$ acyclic olefin and at least one $C_4$-, $C_5$-, $C_6$- or $C_7$-cyclic olefin, wherein the content of at least one of the $C_4$-, $C_5$-, $C_6$- or $C_7$-cyclic olefin in the feed is controlled such that it is at or below a predetermined level.

According to a further aspect, the present invention relates to a process for controlling the level of cycloalkanes and cycloalkenes formed in a process for converting an olefin containing hydrocarbon feed into an oligomerization product or a hydrogenated oligomerization product, said process comprising contacting the feed in a reactor with the oligomerization catalyst under conditions suitable to oligomerize the olefin to obtain an oligomerization product and optionally hydrogenating the oligomerization product, said olefin feed material comprising at least one $C_2$ to $C_{12}$ acyclic olefin and at least one $C_4$-, $C_5$-, $C_6$- or $C_7$-cyclic olefin, wherein the content of at least one of said $C_4$-, $C_5$-, $C_6$- or $C_7$-cyclic olefin in the feed is controlled such that it is at, below or above a predetermined level.

Further and preferred embodiments of the present invention, according to the aspects summarized above, are disclosed in the dependent claims and in the following description including the examples and figures illustrating the present invention.

DETAILED DESCRIPTION OF THE INVENTION

Figure 1:
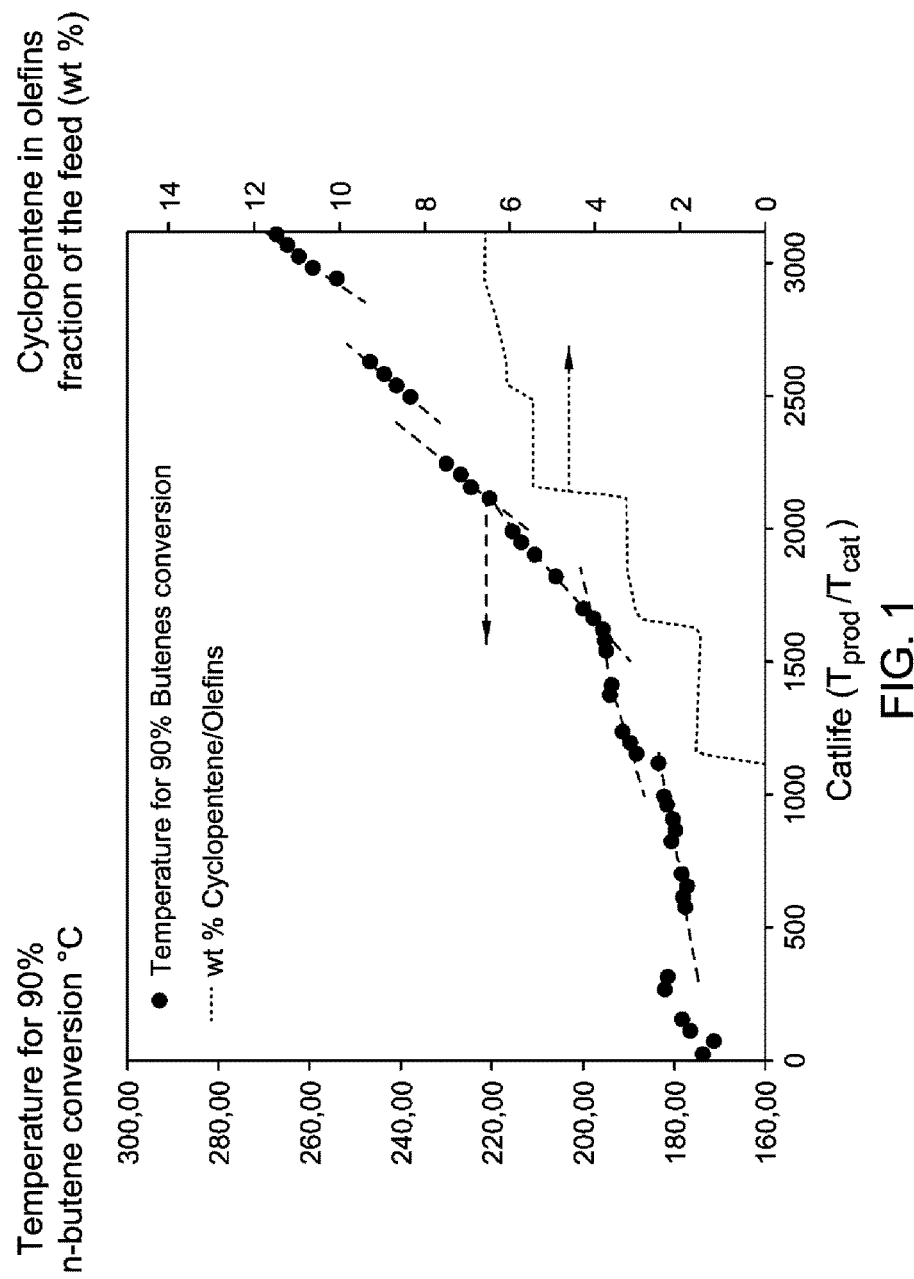
FIG. 1 is a graphic representation of the reactor temperature required for 90% n-butene conversion of the feed as a function of the ratio of the total weight of product produced per total weight of catalyst with increasing cyclopentene content in the olefin fraction of the feed.

Before the materials, compounds, components, compositions and/or processes of the present invention are disclosed in more detail, it is noted that the singular forms "a", "an" and "the" include plural referents unless otherwise specified.

Furthermore, the words "comprising" (and any form of comprising such as "comprise" and "comprises"), "having" (and any form of having, such as "have" and "has"), "including" (and any form of including, such as "includes" and ("include") or "containing" (and any form of containing, such as "contains" and "contain") are inclusive or open-ended and do not exclude additional, unrecited elements such as materials, compounds or compositions or additional process steps.

The terms "feed" and "feedstock" are used herein interchangeably to refer to the olefin containing hydrocarbon feed used in the process of the invention. The stream containing said feed may also be referred to as "olefin feed".

The wording "controlling the content of cyclic olefin(s) in the feed" and any form thereof used herein interchangeably refers to selecting a feed having the predetermined level of cyclic olefin(s) in the feed from existing feeds or adjusting the content of the cyclic olefins in the feed by any method known in the art such as distillation. The process of the invention may therefore also be referred as a process wherein the content of at least one of the $C_4$-, $C_5$-, $C_6$- or $C_7$-cyclic olefin in the feed is at, below or above a predetermined level depending on the aspect of the invention.

In further embodiments of the present invention, compounds, components, compositions and processes as disclosed herein can consist of the features disclosed in these respects.

Hydrocarbon Feed

In accordance with the present invention, the olefin containing hydrocarbon feed to be converted into an oligomerization product or a hydrogenated oligomerization product comprises at least one $C_2$ to $C_{12}$ acyclic olefin and at least one cyclic olefin in which the ring is $C_4$-, $C_5$-, $C_6$- or $C_7$-membered, wherein the content of at least one of the $C_4$-, $C_5$-, $C_6$- or $C_7$-cyclic olefin in the feed is controlled such that it is at, below or above a predetermined level. The olefins may include diolefins.

As used herein, "acyclic olefin" refers to any unsaturated hydrocarbon having the formula $C_nH_{2n}$, wherein C is a carbon atom, H is a hydrogen atom, and n is the number of carbon atoms in the olefin. According to this invention, the acyclic olefins in the feed typically have from 2 to 12 carbon atoms, such as at least 3 and no more than 8 carbon atoms, and typically at least 3 and no more than 6 carbon atoms. They are also referred to as lower or light olefins. According to a preferred embodiment, the feed is a $C_3$, $C_4$ and/or $C_5$ olefin containing stream.

The feed may also comprise one or more paraffins. As used herein, "paraffins" refers to any of the saturated hydrocarbons having the formula $C_nH_{2n+2}$, wherein C is a carbon atom, H is a hydrogen atom, and n is the number of carbon atoms in the paraffin. The paraffins that may be present in the olefin feed typically have from 1 to 25 carbon atoms, such as from 1 to 15 carbon atoms, and conveniently at least 3 and no more than 6 carbon atoms. Examples of suitable paraffins include methane, ethane, propane, butane, pentane, hexane, isomers thereof and mixtures thereof. If present in the feed, the paraffins may have the same or a different number of carbon atoms as the olefins.

If present, the paraffin acts as a diluent. If used, the olefin feed may comprise at least 10 wt %, at least 25 wt %, at least 30 wt %, at least 35 wt %, or at least 40 wt % paraffin, based upon the total weight of the feed. Alternatively stated, if used, the diluent may be present in the olefin feed in the range from 10 wt % to 40 wt %, alternatively, from 10 wt % to 35 wt %, and alternatively from 20 wt % to 35 wt % based upon the total wt of the feed. The diluent may also be fed to the reactor(s) separately from the olefin feed. When fed separately, the diluent may be fed in amounts equivalent to those mentioned above, where the diluent is co-fed with the feed. These amounts may not necessarily be the same as the ranges stated above given that more or less of the diluent may be necessary when fed separately to provide an equivalent.

Additionally, the feed may comprise an oligomer (higher olefin), for example, a dimer, such as one provided by recycling a part of an olefin oligomerization product stream. As used herein, "oligomer(s)" or "oligomer product" refers to an olefin (or a mixture of olefins) made from a few light olefins. For example, oligomers include dimers, trimers, tetramers, obtained from two, three or four light olefins of the same number of carbon atoms, mixed oligomers, obtained from 2 or more olefins having different numbers of carbon atoms and mixtures thereof. In a class of embodiments, "oligomer(s)" refers to an olefin (or a mixture of olefins) having 20 carbon atoms or less, alternatively, 15 carbon atoms or less, such as 10 carbon atoms or less, alternatively, 9 carbon atoms or less, and conveniently, 8 carbon atoms or less, that has been obtained by linking two or more light olefins together. As used herein, "oligomerization process" refers to any process by which light olefins are linked together to form the oligomer(s) as defined above. As used herein, the term "oligomerization conditions" refers to any and all those variations of equipment, conditions (e.g. temperatures, pressures, weight hourly space velocities etc.), materials, and reactor schemes that are suitable to conduct the oligomerization process to produce the oligomer(s) as known and applied in the art and discussed in more detail below.

More specifically, the olefin containing hydrocarbon feed comprises an acyclic olefin selected from the group consisting of $C_3$, $C_4$, $C_5$, $C_6$ olefins and mixtures thereof. Preferably, the acyclic olefin is selected from the group consisting of propene, butenes and pentenes, such as propene, n-butene, i-butene, pentene-1, 2-methyl-1-butene, and 2-methyl-2-butene.

In a class of embodiments, the olefin containing hydrocarbon feed comprises a mixture of acyclic $C_3$ and $C_5$ olefins, a mixture of acyclic $C_4$ and $C_5$ olefins or a mixture of acyclic $C_3$, $C_4$ and $C_5$ olefins.

When feed streams containing the foregoing mixtures of acyclic olefins are used, the ratio of the $C_5$ acyclic olefin to the sum of $C_3$ and $C_5$, $C_4$ and $C_5$ or $C_3$, $C_4$ and $C_5$ olefins may be in the range of from 0.2 to 0.8, such as 0.3 to 0.6 or 0.3 to 0.5 or 0.3 to 0.4, based on weight.

With regard to the total amount of olefins (cyclic+acyclic) present in the feed, in a class of embodiments, the feed comprises 20 wt % or more olefins, such as 25 wt % or more olefins, alternatively 30 wt % or more olefins, such as 35 wt % or more olefins, alternatively 40 wt % or more olefins, such as 45 wt % or more olefins, alternatively 50 wt % or more olefins, such as 55 wt % or more olefins, alternatively, 60 wt % or more olefins, such as 65 wt % or more olefins, alternatively, 70 wt % or more olefins, such as 75 wt % or more olefins, and alternatively, 80 wt % or more olefins, based upon the total weight of the feed. Alternatively, the content of olefins may be in a range derivable from the preceding limits. Ranges of from 60 to 90 wt % or 70 to 80 wt % or 65 to 70 wt % are suitable.

The paraffins and the olefins are the major constituents of the feed and usually are present in an amount of at least 50 wt %, typically at least 75 wt %, such as at least 90 wt % of the total weight of the feed.

According to one embodiment, the olefin containing hydrocarbon feed comprises up to 50 or 60 wt % of butenes and up to 30 or 40 wt % of pentenes, based on the total weight of the feed.

Specific sources for obtaining olefin containing hydrocarbon streams as disclosed above are disclosed in detailed below.

Examples of suitable olefin feeds include refinery streams such as Fluidized Catalytic Cracking (FCC) streams, coker streams, pyrolysis gasoline streams or reformates.

Examples of suitable $C_3$ olefin containing feedstreams include untreated $C_3$ rich refinery streams such as "dilute" or "refinery grade" propylene from a Fluidized Catalytic Cracker (FCC), $C_3$ rich stream from a steam cracker, $C_3$ rich streams from the production of "chemical grade" or "polymer grade" propylene, $C_3$ rich streams from refinery gas recovery units, $C_3$ rich streams from Propane Dehydrogenation Units, $C_3$ rich streams from Gas to Olefin (GTO) Units, or Fisher-Tropsch Units, and $C_3$ rich return streams from polypropylene producing units. The $C_3$ stream from catalytic cracking may, depending on cracking severity, contain for example from 50 to 60 wt % of propylene, or higher such as 65 wt % or more, or 70 wt % or above such as 72 wt % or 75 wt % or even up to 79 wt %. The $C_3$ stream from steam cracking may, depending on its sourcing in the steam cracking product cleanup process, contain from 5 to 95 wt % of propylene, for example 92 to 94 wt % for chemical-grade propylene, or 25 to 50 wt % propylene for a by-product stream from the production of chemical-grade propylene.

Examples of suitable $C_4$ olefin containing feeds include refinery feeds often referred to as Raffinate-1 (RAF-1), Raffinate-2 (RAF-2) or Raffinate-3 (RAF-3). Typically, Raffinate-1, Raffinate-2 and Raffinate-3 may be regarded as streams obtainable at various stages in the processing of crude $C_4$ streams obtained from petroleum refining processes. These streams are usually from olefin steam crackers but may also come from refinery catalytic crackers, in which case they generally contain the same components but in different proportions. The first stage of processing these crude $C_4$ refinery streams is to remove butadiene from these streams, such as by solvent extraction or hydrogenation. Butadiene may be present in the crude $C_4$ refinery streams as 40 to 45 wt % of the stream. The product obtained after butadiene removal is Raffinate-1. It generally consists of isobutylene, the two isomers of n-butane, 1-butene and 2-butene, and smaller quantities of butanes and other compounds. The next step consists in removing isobutylene, usually by reaction of isobutylene with methanol to produce methyl-tert-butylether (MTBE), which then produces Raffinate-2. Raffinate-3 (RAF-3) is less common but may be obtained after separation of 1-butene from Raffinate 2. Raffinate-3 typically has a residual 1-butene content of about 1%.

Examples of suitable $C_5$ olefin feeds include FCC Light Naphtha streams, steam cracker $C_5$ rich streams that have been treated for diene removal, $C_5$ olefin containing streams from Gas to Olefin (GTO) Units, or Fisher-Tropsch Units. These streams may comprise $C_5$ olefin components in the amounts as disclosed hereinabove. For example, an FCC Light Naphtha stream may comprise 20 wt % or more $C_5$ olefins, alternatively, 30 wt % or more $C_5$ olefins, alternatively, and preferably, 40 wt % or more $C_5$ olefins, or 50 wt % or more $C_5$ olefins, based upon the total weight of the feed.

The above feeds are usually subjected to clean-up procedures to remove undesired components such as N-, S-, or O-containing impurities. Methods for removal of said undesired components are known in the art. For example, WO 2013/013884; WO 2013/013885; WO 2013/013886; WO 2013/013887; and WO 2013/013888 disclose procedures based on the use of adsorbers (guard beds) to remove undesired components. WO 2012/078218 discloses a procedure based on solvent extraction suitable to remove undesired components. These and related procedures may be used in the context of the present invention to achieve desired feed purity.

Diolefins (dienes) such as $C_4$, $C_5$, $C_6$ and/or $C_7$ dienes may also be present in the feeds of the present invention. Their level is conveniently controlled by means of methods well-known in the art such as hydrogenation. Typically, the content of diolefins in the feed stream prior to oligomerization is lower than 8000 wt ppm, preferably lower than 5000 wt ppm, more preferably lower than 1000 wt ppm and most preferably lower than 200 wt ppm.

The at least one cyclic olefin the content of which is to be controlled according to the embodiments as disclosed herein is a $C_4$-, $C_5$-, $C_6$- or $C_7$-cyclic olefin. The cyclic olefin ring structure may be substituted or unsubstituted such as substituted with one or more $C_1$- or $C_2$-substituents such as methyl. In particular, the at least one cyclic olefin is selected from the group consisting of cyclobutenes, cyclopentenes, cyclohexenes and cycloheptenes. Preferably, at least one cyclic olefin has a $C_5$ ring structure. In particular, the at least one cyclic olefin is cyclopentene, methyl cyclopentene, methyl cyclobutene, cyclohexene or methyl cyclohexene.

According to an embodiment of the present invention, the predetermined level of the content of the at least one cyclic olefin is selected such that the life of the oligomerization catalyst is increased. By increased catalyst life it is meant that the deactivation rate of the catalyst is reduced by a factor of at least 2, preferably at least 5 as compared to the deactivation rate at another (higher) level of the content of the at least one cyclic olefin. By using the process if this invention it is possible to decrease the deactivation rate by a factor of 8 or even 10.

In particular, the predetermined level of the content of at least one cyclic olefin in the feed may be selected such that the deactivation rate of the catalyst is lower than 30° C., preferably lower than 20° C., more preferably lower than 10° C. per 1,000 ton (t) oligomerization product produced per ton (t) of catalyst, in particular lower than 20° C. or 10° C. per 1,000 ton (t) oligomerization product produced per ton (t) of catalyst, wherein the deactivation rate of the catalyst is defined as the temperature increase needed to maintain 90% conversion of selected olefin(s) in the feed.

According to an embodiment of the present invention, the content of the at least one cyclic olefin in the feed is used to control the composition of the oligomerization product or hydrogenated oligomerization product, in particular the content of $C_6$ to $C_{16}$ cycloalkanes and cycloalkenes in the oligomerization product. For example, the content of the at least one cyclic olefin in the olefin containing hydrocarbon feed may be less than 2 wt %, such as 1.9, 1.8, 1.7, 1.6, 1.5, 1.4, 1.3, 1.2, 1.0, 0.9, 0.8, 0.7, 0.6, 0.5, 0.4, 0.3, 0.2, or 0.1 wt %, based on the total weight of olefins in the feed material. Preferably, the at least one cyclic olefin has a five-membered ring structure. In particular, the at least one cyclic olefin is cyclopentene. It has be found that a deactivation rate below 20° C. per 1,000 ton (t) of oligomerization product can be maintained by adjusting the content of cyclopentene in the feed subjected to catalytic oligomerization at a level at or below 1.5 wt % based on the total weight of olefins in the feed.

According to another embodiment, the predetermined level of the content of the at least one cyclic olefin is selected such the content of $C_6$ to $C_{16}$ cycloalkenes and cycloalkanes formed in the oligomerization product is at, below or above a predetermined level, in particular below 15 wt %, preferably below 5 wt %, in particular below 2 wt %, based on the total weight of the reactor effluent containing the oligomerization product. As used herein, reactor effluent refers to the stream after contacting the oligomerization catalyst, without further treatment steps carried out, except for distillation/fractionation to determine the composition of the reacted feed.

The predetermined level of the content of the at least one cyclic olefin may be selected based on the following correlation:

$$A \text{ (wt \%)} = 0.25 + 1.93(B \text{ (wt \%)})$$

wherein A is the content of $C_n$ to $C_{n+10}$ cycloalkanes and cycloalkenes formed in the oligomerization product, based on the total weight of the reactor effluent containing the oligomerization product, B is the content of a cyclic olefin having n−1 carbon atoms present in the olefin feed, based on the total weight of olefins in the feed and n is an integer from 5 to 8, preferably, n is 6.

In particular, the correlation between the level of cyclopentene in the hydrocarbon feed (B') and the content of $C_6$ to $C_{16}$ cycloalkenes in the oligomerization product (A') is as follows:

$$A' \text{ (wt \%)} = 0.25 + 1.93(B' \text{ (wt \%)}).$$

Such correlation can be used to calculate the level of cyclopentene required to produce oligomerization product with a desired amount of $C_6$ to $C_{16}$ cycloalkenes.

Controlling the level of the at least one cyclic olefin can be achieved by distillation or dilution operations on the streams as disclosed in detail above. These operations as such are well-known in the art.

Oligmerization

The oligomerization is carried out by contacting the feed in a reactor with an oligomerization catalyst under conditions suitable to oligomerize the olefin to obtain an oligomerization product and optionally hydrogenating the oligomerization product, wherein the oligomerization catalyst is usually selected from the group consisting of zeolite and phosphoric acid-based catalysts.

The catalysts utilized in the oligomerization processes may be any suitable zeolite catalyst(s) capable of oligomerizing olefins. Exemplary methods and materials are provided in WO 2012/033562, U.S. Pat. No. 4,973,790, and US-A-2012/0022224. Zeolites are the aluminosilicate members of the family of microporous solids known as "molecular sieves." The term molecular sieve refers to a particular property of these materials, i.e., the ability to selectively sort molecules based primarily on a size exclusion process. This is due to a very regular pore structure of molecular dimensions. The maximum size of the molecular or ionic species that can enter the pores of a zeolite is controlled by the dimensions of the channels. These are conventionally defined by the ring size of the aperture, where, for example, the term "8-ring" refers to a closed loop that is built from 8 tetrahedrally coordinated silicon or aluminum atoms and 8 oxygen atoms. These rings are not always perfectly symmetrical due to a variety of effects, including strain induced by the bonding between units that are needed to produce the overall structure, or coordination of some of the oxygen atoms of the rings to cations within the structure. Therefore, the pores in many zeolites may not be cylindrical.

The at least one zeolite catalyst suitably includes a medium pore size molecular sieve having a Constraint Index of about 1 to about 12. Constraint Index and a method of its determination are described in, for example, U.S. Pat. No. 4,016,218.

Examples of the at least one zeolite catalyst include those of the TON structure type (for example, ZSM-22, ISI-1, Theta-1, Nu-10, and KZ-2), those of the MTT structure type (for example, ZSM-23 and KZ-1), those of the MFI structure type (for example, ZSM-5, ZSM-5b, etc.), those of the MFS structure type (for example, ZSM-57), those of the MEL-structure type (for example, ZSM-11), those of the MTW structure type (for example, ZSM-12), those of the EUO structure type (for example, EU-1), those of the AEL structure type (for example, SAPO-11), members of the ferrierite family (for example, ZSM-35) and members of the ZSM-48 family of molecular sieves (for example, ZSM-48). Other examples include MWW (e.g., MCM-22, MCM-48), MOR, or beta type catalysts. As used herein, the term "structure type" is used as described in the Structure Type Atlas, Zeolites 17, 1996.

Preferably, the at least one zeolite catalyst is selected from at least one of ZSM-5, ZSM-5b, ZSM-11, ZSM-12, ZSM-18, ZSM-22, ZSM-23, ZSM-35, ZSM-38, ZSM-48, ZSM-50, ZSM-57, and mixtures thereof. The at least one zeolite catalyst comprises molecular sieves having pores formed by 10-membered rings of tetrahedrally coordinated atoms, such as molecular sieves having the TON or MFS structure type.

Mixtures of two or more of catalysts may be used in the processes of the present invention. For example, the mixture may include ZSM-22 and ZSM-57 or ZSM-22 and ZSM-5 or ZSM-57 and ZSM-5. The at least one zeolite catalyst may also be combined with other catalysts such as a solid phosphoric acid (sPa) catalyst or other acid catalysts.

The zeolite used in the oligomerization catalyst may have an average crystallite or particle size of up to 15 µm, such as within the range of from 0.01 to 6 µm, alternatively, from 0.05 to 5 µm, and alternatively, from 0.1 to 3 µm. As used herein, "average particle size" refers to the arithmetic average of the diameter distribution of the crystals on a volume basis.

Preferably, the zeolite is used in its proton, or acidic form. To obtain this form, an as-synthesized molecular sieve that has been obtained in an alkaline or alkaline-metal form is advantageously converted to its acid form, for example, by acid treatment, e.g., by HCl, acetic acid, etc. or by ion exchange, for example, ammonium ion exchange. Subsequently, it may undergo calcination before use. The calcined materials may be post-treated, such as by steaming.

The at least one zeolite catalyst may be produced by any suitable method known for the given type of zeolite. One technique includes heating a reaction mixture containing a source of silicon oxide, a source of aluminum oxide and, if appropriate, an organic promoter, for example, a nitrogen or phosphorus-containing organic base, together optionally, with an alkali metal base, and separating the porous aluminosilicate crystals (zeolite precursor crystals) formed. The precursor crystals are then calcined in air or oxygen at a temperature exceeding or about 500° C., for example, at a temperature of 550° C. for about 10 to about 20 hours. As recognized in the art, calcination temperatures and durations may vary depending on the type of zeolite catalyst or combination of zeolite catalysts selected. In one embodiment, the calcined material is exchanged with ammonium ions (NH4+) and subjected to conditions under which the ammonium ions decompose, with the formation of ammonia and a proton, thus, producing an acidic form of the at least one zeolite catalyst. Alternatively, the acidic form of the catalyst may be obtained by acid exchange with hydrochloric acid, acetic acid, etc. If desired, however, the calcined material may be used as a catalyst without first being exchanged with ammonium ions, since the material already possesses acidic sites.

Ammonium exchanged and calcined monodimensional 10-rings zeolites (e.g., ZSM-22 and ZSM-23) may be treated to selectivate their surface, thereby, forming a selectivated catalyst. This selectivation may be achieved in numerous ways. In an embodiment, the at least one zeolite catalyst may be titrated with an organic nitrogen base, such as collidine. See, for example, U.S. Pat. No. 5,026,933. Another example is by depositing a crystalline Si:Al layer on a core of zeolite where this layer has a higher Si:Al ratio than the untreated zeolite. See, for example, U.S. Pat. No. 6,013,851.

Although much of the discussion above is directed to aluminosilicate zeolites, it is possible to use material in which silicon and aluminum have been replaced in whole or in part by other elements, for example, any one or more of a Group 2 to Group 15 atom. For example, silicon may be replaced by or contacted with germanium and aluminum or may be replaced with boron, gallium, chromium, and iron. As used herein, these materials containing such replacement lattice elements may also be termed zeolites.

It may be desirable to incorporate the molecular sieves or zeolites mentioned above with another material that is resistant to the temperatures and other conditions employed in the olefin oligomerization process. Thus the molecular sieves or zeolites may be used in the form of an extrudate with binder, where the molecular sieve or zeolite is dispersed within a conventional binder. Binding is typically done by forming a pill, sphere, or extrudate. The extrudate is usually formed by extruding the molecular sieve, optionally in the presence of a binder, and drying and calcining the resulting extrudate. The binder materials used are resistant to the temperatures and other conditions, e.g., mechanical attrition, which occur in various hydrocarbon conversion processes.

Examples of binder materials that may be employed with the molecular sieves or zeolites suitable for use in the process of the invention include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Naturally occurring clays which may be used include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or after being subjected to calcination, acid treatment or chemical modification. Examples of other materials include porous matrix materials such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Alternatively, a binder free version of the zeolite may be used.

Exemplary catalyst materials and processes for making such catalysts may also be found in U.S. Pat. Nos. 3,960,978, 4,016,218, 4,021,502, 4,381,255, 4,560,536, 4,919,896, 5,446,222, 5,672,800, 6,143,942, 6,517,807, 6,884,914, US-A-2006/0199987, EP-A-0 746 538, WO 1994/12452 WO 2005/118512, WO 2005/118513, WO 2007/006398, and WO 2008/088452. See also "Atlas of Zeolite Structure Types," Eds. W. H. Meier, D. H. Olson and Ch. Baerlocher, Elsevier, Fourth Edition, 1996.

The oligomerization catalyst used in the process according to this invention as described above is most preferably selected from the group consisting of zeolites having MFS and TON structure, in particular ZSM-57 and ZSM-22 and mixtures thereof.

In the context of oligomerization, suitable reaction conditions may include temperatures from about 80° C. to about 350° C. Close to and above the upper end of the range, deoligomerization rates increase and may predominate over the oligomerization reaction providing an upper limit to practical operation. More typically, the reaction temperature is from about 130° C. to about 320° C., preferably from about 135° C. to about 310° C., and even more preferably from about 160° C. to about 270° C.

More specifically, the pressure may be in the range of from about 400 psig to about 4000 psig (2860 to 27688 kPa), and alternatively, from about 500 psig to about 1500 psig (3550 to 10446 kPa).

The olefin weight hourly space velocity based on catalyst, may be in the range of from about 0.1 $hr^{-1}$ to about 20 $hr^{-1}$ or from about 0.5 $hr^{-1}$ to about 5 $hr^{-1}$.

In one embodiment, the process is conducted at a temperature of 80-350° C.; an olefin weight hourly space velocity of 0.1-20 $hr^{-1}$, and a pressure of 2860-27688 kPa.

In another embodiment, the process is conducted at a temperature of 130-320° C.; an olefin weight hourly space velocity of 0.5-5 $hr^{-1}$; and a pressure of 3550-10446 kPa.

Optionally, the olefin feed may also be hydrated (i.e., contacted with water) prior to oligomerization. In an embodiment, sufficient water is used to saturate the feed. In particular, the feed may comprise from about 0.01 to about 0.25, alternatively, from about 0.02 to about 0.20, and alternatively, from about 0.03 to about 0.10, mol % water based on the total hydrocarbon content of the feed. If desired and by way of example, the water content of the feed may be increased by passage through a thermostated water saturator. The olefin feed used in the oligomerization step can therefore be wet or dry.

In further embodiments, the materials and conditions as disclosed in US-A-2007/0255081 and US-A-2012/0116141 may be used. In this respect, the summaries of the disclosures of these two references as provided in the Background section hereinabove are fully incorporated into this paragraph by reference.

Oligomerization Products

In general, the oligomerization product comprises $C_5$ to $C_{20}$ olefins boiling in the range of 30° C. to 310° C., in particular oligomerization products selected from the group consisting of pentenes, hexenes, heptenes, octenes, nonenes, decenes, undecenes, dodecenes and tridecenes as shown in the following table.

| Oligomer Products | Distillation Range (° C.) ASTM D1078 | |
|---|---|---|
| | Initial Boiling Point | Dry Point |
| Pentenes | 30 | |
| Hexenes | 35 | 72 |
| Heptenes | 88 | 97 |
| Octenes | 114 | 126 |
| Nonenes | 135 | 143 |
| Decenes | 155 | 160 |
| Undecenes | 167 | 178 |
| Propylene Tetramers or Dodecenes | 175 | 225 |
| Tridecenes | 204 | 213 |
| Heavy Tridecenes | 215 | 260 |

The level of cycloalkenes and cycloalkanes containing 6 or more carbon atoms in the oligomerization product may preferably be in the range below 2% or lower such as 1%, 0.5% or lower.

The oligomer products are useful in many applications and are the starting material for further processes. For example, the oligomer product may be polymerized to produce polyolefins that have application in the plastics industry and synthetic basestocks for lubricants. The oligomer product may be used in alkylation reactions for the production of surfactants. The oligomer products may be reacted with sulphur containing compounds to produce mercaptans. The oligomer product may undergo hydroformylation and subsequently hydrogenation to produce alcohols. The alcohols may be used in industry such as, for example, solvents, or be incorporated into the production of detergents/surfactants. The alcohols may further be used in many other areas of industry such as, for example, undergoing esterification to produce esters that have application as plasticizers. Oligomer products may be hydrogenated to produce a predominately paraffin product such as ISOPAR™.

In a class of embodiments, wherein the oligomerization product has an initial boiling point (IBP) in the range of from 35° C. to 230° C., i.e. between 35° C. to 230° C. and a distillation range, dry point (DPT) determined in accordance with ASTM D86 in the range of from 72° C. to 260° C., i.e., between 72° C. to 260° C.

As noted above, the oligomerization product may be further processed by distillation and hydrogenation to obtain a hydrogenated oligomerization product.

In general, the hydrogenated oligomerization product has an initial boiling point (IBP) in the range of from 98 to 270° C., i.e. between 98 to 270° C. and a distillation range; dry point (DPT) in the range of from 104 to 311° C., i.e. between 104 to 311° C.

According to one embodiment, the oligomerization product has an initial boiling point (IBP) of 153° C. and a distillation range, dry point (DPT) of 173° C. After hydrogenation, the hydrogenated oligomerization product has an IBP of 162° C. and a DPT of 177° C.

According to one embodiment, the oligomerization product has an initial boiling point (IBP) of 177° C. and a distillation range, dry point (DPT) of 188.5° C., determined in accordance with ASTM D86. After hydrogenation, the hydrogenated oligomerization product has an IBP of 181° C. and a DPT of 193° C.

According to one embodiment, the oligomerization product has an initial boiling point (IBP) of 185° C. and a distillation range, dry point (DPT) of 208° C., determined in accordance with ASTM D86. After hydrogenation, the hydrogenated oligomerization product has an IBP of 190° C. and a DPT of 210° C.

According to one embodiment, the oligomerization product has an initial boiling point (IBP) of 217° C. and a distillation range, dry point (DPT) of 260° C., determined in accordance with ASTM D86. After hydrogenation, the hydrogenated oligomerization product has an IBP of 223° C. and a DPT of higher than 260° C.

EXAMPLES

Example 1: Control of Catalyst Deactivation Rate

This example illustrates oligomerization of a cyclopentene containing hydrocarbon stream consisting of mixed $C_4$ and $C_5$ olefins and paraffins and control of catalyst deactivation rate by controlling the level of cyclopentene in the feed.

A mixture of $C_4$ and $C_5$ olefins diluted in $C_4$ and $C_5$ paraffins was reacted in an isothermal fixed bed reactor over a ZSM-57 based zeolite catalyst sample at 70 barg and 180-260° C. at 3 $h^{-1}$ weight-hourly-space-velocity (WHSV) with increasing concentrations of cyclopentene. The ZSM-57 based catalyst used in the examples of this description contains about 50 wt % ZSM-57 zeolite powder and about 50 wt % alumina binder. Table 1 presents the chemical composition of the different reactant mixtures used in this example.

The reaction was kept at constant total n-butenes conversion of 90% by changing the reactor temperature. FIG. 1 shows the reactor temperature required for 90% n-butenes conversion as a function of the ratio of the total weight of product produced per total weight of catalyst.

As noted in the foregoing description, the catalyst deactivation rate is defined herein as the temperature increase needed to maintain 90% total butenes conversion, per 1000 tonnes product produced per tonne of catalyst. The deactivation rates were calculated for the different cyclopentene contents from the slope of the relevant regions of the curve shown in FIG. 1.

Figure 2:
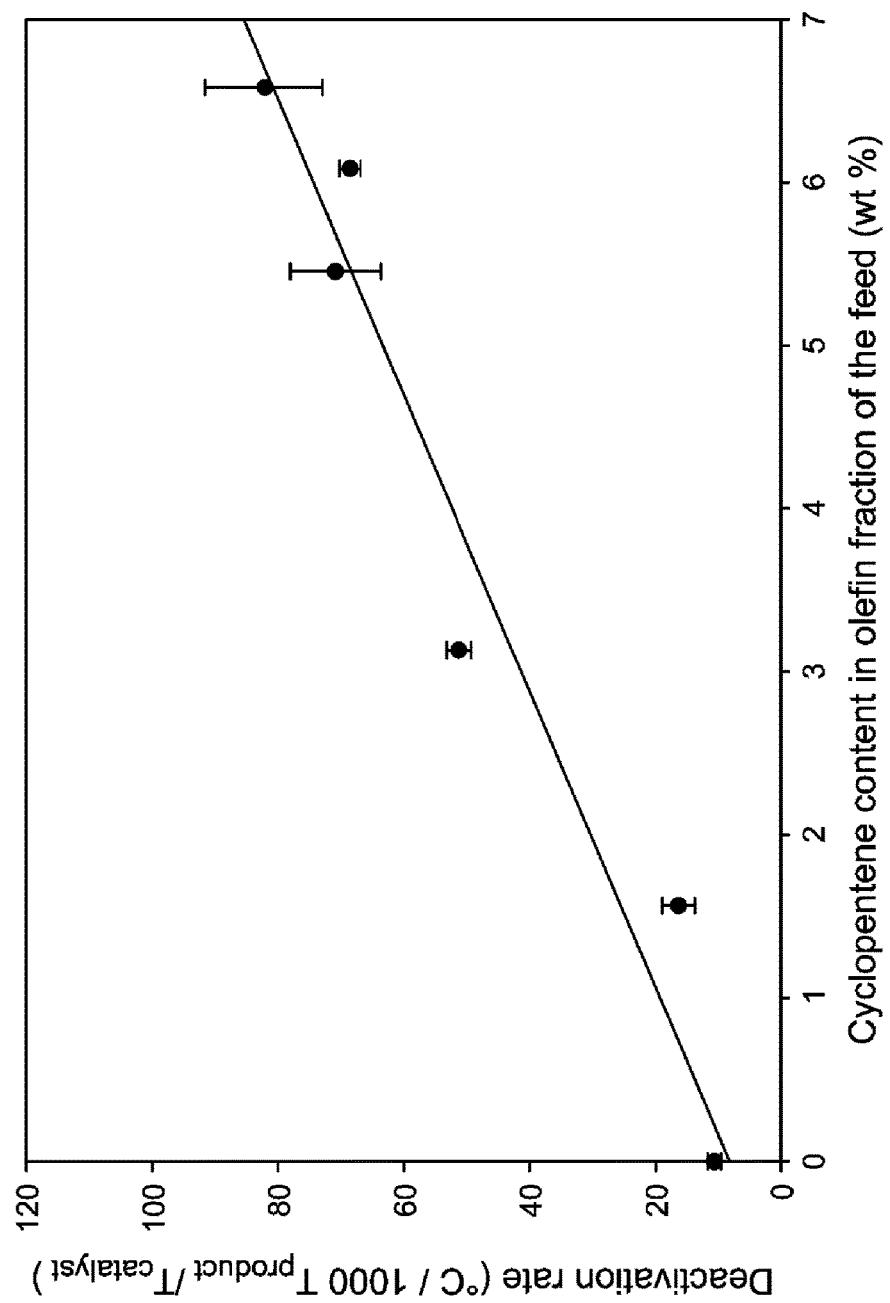
FIG. 2 is a graphic representation of catalyst deactivation rate as a function of cyclopentene content in the olefin fraction of the feed.

The result is shown in FIG. 2 which graphically depicts catalyst deactivation rate as a function of cyclopentene content in the reactive olefin fraction, i.e., the fraction consisting of 1-butene, isobutene, pentene-1, 2-methylbutene-2, 2-methylbutene-2 and cyclopentene referred to as "olefinic content" in Table 1. Error bars indicate standard error in the measured deactivation rates. An increase in cyclopentene content leads to a linear increase in the catalyst deactivation rate. Specifically, as can be seen from the graph, an increase in cyclopentene content from 1 to 6 wt % results in an increase in deactivation rate from ~20 to ~80° C. per 1000 T product/T catalyst.

Example 2

This example illustrates oligomerization of a cyclopentene containing hydrocarbon stream consisting of mixed $C_4$ and $C_5$ olefins and paraffins and control of the formation of cycloalkanes and cycloalkenes in the oligomerization product.

A mixture of $C_4$ and $C_5$ olefins, containing different concentrations of cyclopentene and diluted in $C_4$ and $C_5$ paraffins was reacted in an isothermal fixed bed reactor over a ZSM-57 based zeolite catalyst sample at 70 barg and 180-260° C. at 3 $h^{-1}$ weight-hourly-space-velocity (WHSV). The reaction was maintained at constant total n-butene conversion of 90% by adjusting the reactor temperature. Table 2 presents the chemical composition of the different reactant mixtures applied in this example.

TABLE 1

Composition Of The Hydrocarbon Feeds Used
(bold face indicates reactive olefins)

| Component | Feed 1 | Feed 2 | Feed 3 | Feed 4 | Feed 5 | Feed 6 |
|---|---|---|---|---|---|---|
| i-Butane | 6.2 | 6.1 | 4.5 | 3.8 | 3.8 | 4.7 |
| n-Butane | 16.3 | 16.8 | 16.9 | 15.2 | 16.0 | 23.2 |
| 1-Butene | 42.3 | 41.7 | 41.8 | 45.2 | 41.9 | 42.0 |
| i-Butene | 0.8 | 1.0 | 1.0 | 1.0 | 1.0 | 1.0 |
| i-Pentane | 0.2 | 0.1 | 0.3 | 0.3 | 0.3 | 0.3 |
| n-Pentane | 11.8 | 11.3 | 11.8 | 10.9 | 11.7 | 8.8 |
| Pentene-1 | 10.3 | 10.2 | 10.0 | 9.2 | 9.8 | 7.3 |
| 2-Me-butene-1 | 0.1 | 0.1 | 0.1 | 0.1 | 0.1 | 0.1 |
| 2-Me-butene-2 | 12.0 | 11.7 | 11.4 | 10.5 | 11.2 | 8.5 |
| Cyclopentene | 0.0 | 1.0 | 2.2 | 3.8 | 4.2 | 4.1 |
| Olefinic content (wt %, incl. Cyclopentene) | 65.5 | 65.7 | 66.5 | 69.8 | 67.4 | 63.0 |
| Cyclopentene content of the olefin fraction (wt %) | 0.0 | 1.5 | 3.3 | 5.4 | 6.2 | 6.5 |

TABLE 2

Composition Of The Hydrocarbon Feeds Used
(bold face indicates reactive olefins)

| | Cyclopentene level | | | | | |
|---|---|---|---|---|---|---|
| | Level 0 | Level I | Level II | Level III | | |
| Component | Feed 1 | Feed 2 | Feed 3 | Feed 4* | Feed 5* | Feed 6* |
| i-Butane | 6.2 | 6.1 | 4.5 | 3.8 | 3.8 | 4.7 |
| n-Butane | 16.3 | 16.8 | 16.9 | 15.2 | 16.0 | 23.2 |
| 1-Butene | 42.3 | 41.7 | 41.8 | 45.2 | 41.9 | 42.0 |
| i-Butene | 0.8 | 1.0 | 1.0 | 1.0 | 1.0 | 1.0 |
| i-Pentane | 0.2 | 0.1 | 0.3 | 0.3 | 0.3 | 0.3 |
| n-Pentane | 11.8 | 11.3 | 11.8 | 10.9 | 11.7 | 8.8 |
| Pentene-1 | 10.3 | 10.2 | 10.0 | 9.2 | 9.8 | 7.3 |
| 2-Me-butene-1 | 0.1 | 0.1 | 0.1 | 0.1 | 0.1 | 0.1 |
| 2-Me-butene-2 | 12.0 | 11.7 | 11.5 | 10.5 | 11.2 | 8.5 |
| Cyclopentene | 0.0 | 1.0 | 2.1 | 3.8 | 4.2 | 4.1 |
| Olefinic content (wt %, incl. Cyclopentene) | 65.5 | 65.7 | 66.5 | 69.8 | 67.4 | 63.0 |
| $C_5^-/(C_4^- + C_5^-)$ ratio | 0.34 | 0.35 | 0.36 | 0.34 | 0.38 | 0.32 |
| Cyclopentene in the olefinic fraction (wt %) | 0.0 | 1.6 | 3.1 | 5.4 | 6.2 | 6.5 |

*Products from these feeds are considered level III products and were blended into one distillation feed. The average level III feed Cyclopentene concentration was of 6.2 wt %.

Table 3 shows the carbon number distribution of the reactor effluents accumulated during operation at each level of cyclopentene. The carbon number distribution was obtained by gas chromatography (PONA analyses), as is well-known in the art. Before analysis, the sample was hydrogenated in the injector of the gas chromatograph.

TABLE 3

Carbon number distribution of the stabilized reactor effluents accumulated at the various cyclopentene levels

| Carbon Number | Cyclopentene Level | | | |
|---|---|---|---|---|
| | 0 | I | II | III |
| $C_6$ | 0.3 | 0.6 | 0.8 | 1.3 |
| $C_7$ | 0.4 | 0.6 | 0.7 | 1.2 |
| $C_8$ | 29.8 | 32.3 | 33.3 | 38.7 |
| $C_9$ | 36.0 | 32.9 | 32.7 | 30.0 |
| $C_{10}$ | 8.3 | 8.0 | 8.8 | 8.9 |
| $C_{11}$ | 2.0 | 2.5 | 2.6 | 2.9 |
| $C_{12}$ | 8.7 | 8.3 | 7.2 | 5.6 |
| $C_{13}$ | 6.3 | 6.1 | 5.6 | 4.6 |
| $C_{14}$ | 2.0 | 2.2 | 2.3 | 2.3 |
| $C_{15}$ | 1.9 | 1.9 | 1.6 | 1.2 |
| $C_{16}$ | 1.3 | 1.2 | 1.0 | 0.6 |
| $C_{17}$ | 1.3 | 1.2 | 1.0 | 0.7 |
| $C_{18}$ | 1.1 | 1.2 | 1.2 | 0.9 |
| $C_{18+}$ | 0.6 | 1.1 | 1.2 | 1.0 |

The reactor effluent collected at each cyclopentene level separately was fractionated in a 15/5 distillation column. The cycloalkanes and cycloalkenes content of the separate distillation fractions was carried out using Gas Chromatography/Mass Spectrometry (GC/MS) (PINA analysis), as is well-known in the art. By using mass spectrometry for GC eluate detection, specific, characteristic masses of cycloalkanes and cycloalkenes molecules can be identified and quantified.

Figure 3:
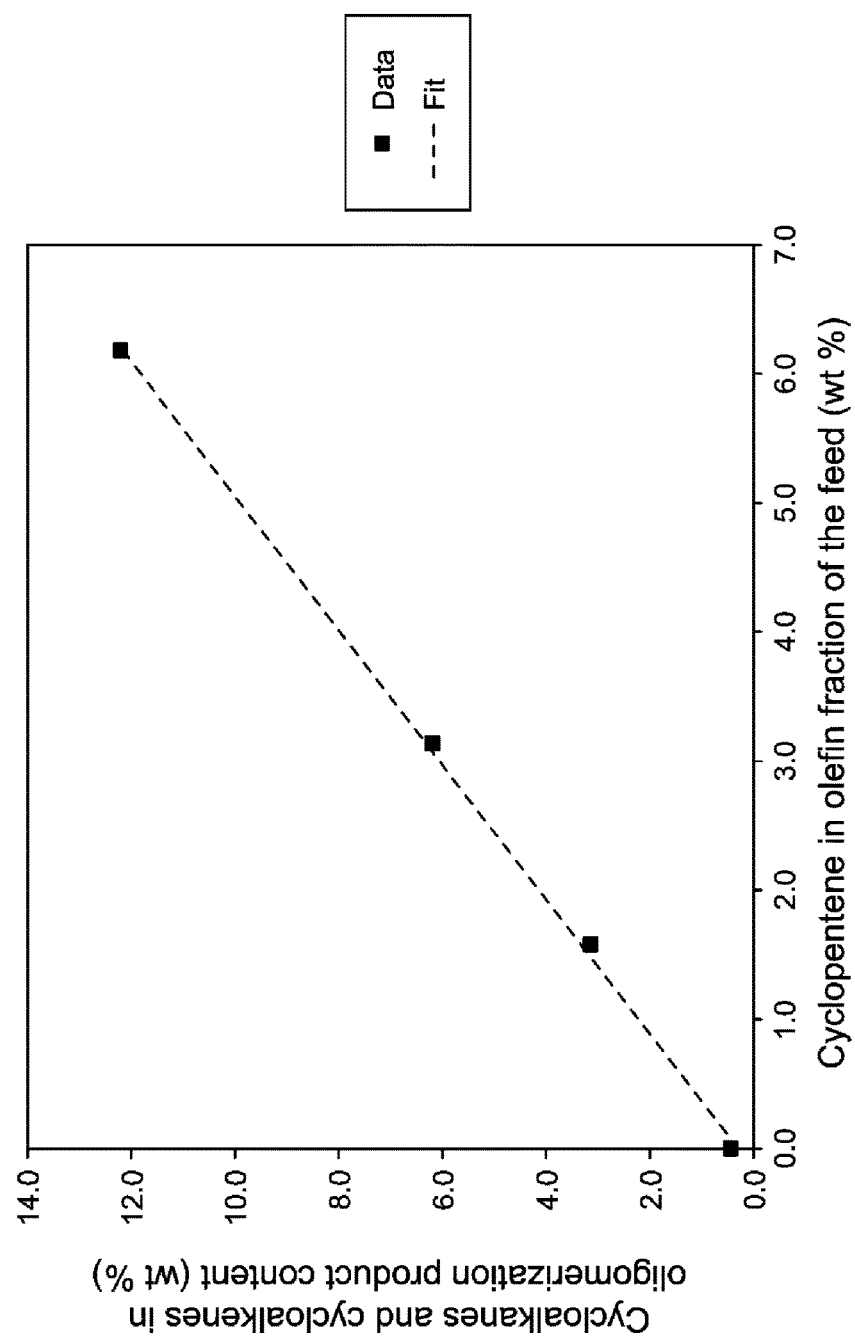
FIG. 3 is a graphic representation of the fraction of cycloalkanes and cycloalkenes in the reactor effluent as function of the cyclopentene content in the olefin fraction of the feed.

Table 4 and FIG. 3 summarize the correlation between the total reactor effluent cycloalkanes and cycloalkenes content and cyclopentene content in the olefinic fraction of the feed.

TABLE 4

$C_6$-$C_{16}$ Naphthenics Content In The Reactor Effluents Collected At The Various Levels Of Cyclopentene

| Cyclopentene level | Cyclopentene in olefins (wt %) | $C_6$-$C_{16}$ cycloalkanes and cycloalkenes (wt %) |
|---|---|---|
| Level 0 | 0.00 | 0.44 |
| Level I | 1.58 | 3.11 |
| Level II | 3.14 | 6.19 |
| Level III | 6.17 | 12.24 |

Based on the data as shown in Table 4 and FIG. 3, it was determined that the cycloalkanes and cycloalkenes content correlates with cyclopentene content by:

$$\text{cycloalkanes and cycloalkanes (wt \%)} = 0.25 + 1.93 * \text{cyclopentene in olefins (wt \%)}.$$

Figure 4:
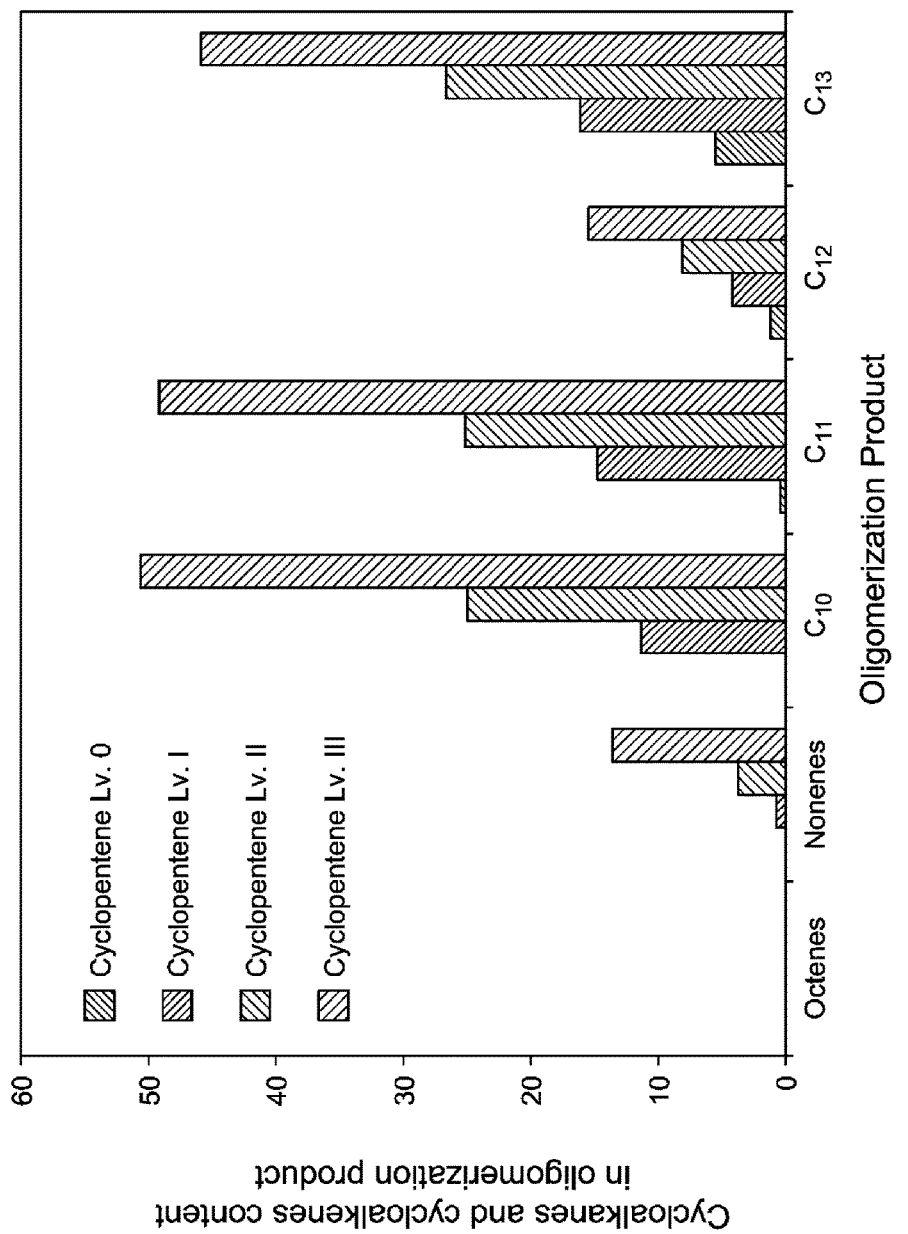
FIG. 4 is a bar diagram showing the content of cyclic hydrocarbons in different carbon number range fractions of the reactor effluent as function of the cyclopentene content in the olefin fraction of the feed.

Table 5 summarizes the cycloalkanes and cycloalkenes content and other important properties of the distillation fractions obtained after fractionation of the reactor effluents at the four different cyclopentene levels. The table indicates which distillation fractions would typically be blended into which final higher olefins products. FIG. 4 shows the cycloalkanes and cycloalkenes content of the final higher olefin products at each level of cyclopentene. The values were calculated by combination of the cycloalkanes and cycloalkenes data of the distillation fractions presented in Table 5.

TABLE 5

Distillation fraction analysis overview.

| | | Level 0 | | | Level I | | | Level II | | | Level III | | |
|---|---|---|---|---|---|---|---|---|---|---|---|---|---|
| Product** | Fraction | Av. CN | Density (g cm$^{-3}$) | N.C.* | Av. CN | Density (g cm$^{-3}$) | N.C.* | Av. CN | Density (g cm$^{-3}$) | N.C.* | Av. CN | Density (g cm$^{-3}$) | N.C.* |
| Lights | Fr 01 | 4.98 | 0.6351 | N/D | 5.05 | 0.6400 | N/D | 5.00 | 0.6374 | N/D | 5.05 | 0.6439 | N/D |
| | Fr 02 | 6.95 | 0.6353 | N/D | 6.83 | 0.6941 | N/D | 6.85 | 0.6967 | N/D | 6.74 | 0.7004 | N/D |
| Octenes | Fr 03-1 | 7.99 | 0.7282 | N/D | 7.97 | 0.7272 | N/D | 8.00 | 0.7284 | N/D | 7.97 | 0.7255 | N/D |
| | F03-2 | 8.16 | 0.7337 | N/D | 8.16 | 0.7332 | N/D | 8.25 | 0.7346 | N/D | 8.10 | 0.7312 | N/D |
| | Fr 04 | 8.51 | 0.7374 | 0 | 8.48 | 0.7370 | 0 | 8.49 | 0.7373 | 0 | 8.44 | 0.7358 | 0 |
| | Fr 05 | 8.71 | 0.7398 | 0 | 8.66 | 0.7392 | 0 | 8.69 | 0.7394 | 0 | 8.68 | 0.7391 | 0 |
| Nonenes | Fr 06 | 8.81 | 0.7412 | 0 | 8.81 | 0.7412 | 0 | 8.82 | 0.7412 | 0 | 8.81 | 0.7407 | 0 |
| | Fr 07-1 | 8.96 | 0.7453 | 0 | 8.93 | 0.7452 | 0 | 8.98 | 0.7459 | 0 | 8.93 | 0.7452 | 1.2 |
| | Fr 07-2 | 9.20 | 0.7506 | 0 | 9.24 | 0.7516 | 1.3 | 9.27 | 0.7548 | 10.6 | 9.24 | 0.7582 | 26 |
| C$_{10}$ | Fr 08 | 9.89 | 0.7569 | 0 | 9.89 | 0.7614 | 9.1 | 9.85 | 0.7663 | 21.7 | 9.89 | 0.7800 | 48.6 |
| Isopar G | Fr 09 | 10.02 | 0.7596 | 0 | 9.98 | 0.7643 | 11.2 | 9.97 | 0.7700 | 25.8 | 9.98 | 0.7832 | 51.2 |
| | Fr 10 | 10.13 | 0.7668 | 0 | 10.18 | 0.7699 | 18.6 | 10.15 | 0.7774 | 33.2 | 10.18 | 0.7908 | 58 |
| C$_{11}$ | Fr 11 | 10.27 | 0.7631 | 0 | 10.18 | 0.7723 | 21.9 | 10.36 | 0.7782 | 34.8 | 10.18 | 0.7916 | 65.7 |
| Isopar H | Fr 12 | 10.81 | 0.7674 | 0.2 | 10.92 | 0.7748 | 17.9 | 10.95 | 0.7800 | 24.7 | 10.92 | 0.7920 | 45.3 |
| | Fr 13 | 11.42 | 0.7730 | 0.9 | 11.38 | 0.7755 | 7.6 | 11.45 | 0.7799 | 13 | 11.38 | 0.7882 | 27.3 |
| C$_{12}$ | Fr 14 | 11.88 | 0.7779 | 0.8 | 11.91 | 0.7792 | 2.9 | 11.90 | 0.7807 | 6 | 11.91 | 0.7836 | 11.5 |
| Isopar L | Fr 15 | 12.51 | 0.7843 | 1.2 | 12.52 | 0.7865 | 5.2 | 12.49 | 0.7878 | 9.4 | 12.52 | 0.7900 | 18.5 |
| C$_{13}$ | Fr 16 | 13.33 | 0.7911 | 3.5 | 13.41 | 0.7977 | 14.4 | 13.36 | 0.8021 | 24.2 | 13.41 | 0.8092 | 43 |
| Isopar N | Fr 17 | 14.87 | 0.8029 | 9.7 | 14.72 | 0.8093 | 19.4 | 14.82 | 0.8148 | 32.1 | 14.72 | 0.8257 | 52.4 |
| Final | Fr 18 | 16.15 | 0.8094 | 12.5 | 16.00 | 0.8133 | 20.8 | 16.08 | 0.8213 | 35.6 | 16.00 | 0.8322 | 54 |

*N.C. = cycloalkanes and cycloalkenes Content from PINA (GC/MS)
**as obtained after oligomerization prior to hydrogenation The above results show there is a clear increase in the concentration of naphthenics of all higher olefin products with increasing level of cyclopentene. The Isopar G, H and N fractions show the highest response to an increase in feed cyclopentene content. Isopar L (mainly C$_{12}$) and Nonene (C$_9$) show relatively low responses to an increase in cyclopentene level as the naphthenics that are formed from the reaction of cyclopentene and C$_4$ olefins (i.e. C$_9$, C$_{10}$, C$_{13}$, C$_{14}$, C$_{15}$, C$_{17}$, etc.) do not boil in the boiling point range of these products.

The invention claimed is:

1. A process for converting an olefin-containing hydrocarbon feed into an oligomerization product, the process comprising the steps of:
    (a) contacting the olefin-containing hydrocarbon feed in a reactor with an oligomerization catalyst having a deactivation rate of below 20° C. per 1,000 ton (t) of oligomerization product under conditions suitable to oligomerize the olefin to obtain a reactor effluent, the olefin-containing hydrocarbon feed comprising at least one C$_2$ to C$_{12}$ acyclic olefin and cyclopentene, the reactor effluent comprising an oligomerization product which comprises C$_6$ to C$_{16}$ cycloalkenes,
    wherein the deactivation rate of the oligomerization catalyst is defined as the temperature increase needed to maintain 90% conversion of the selected at least one acyclic olefin(s) in the feed per 1,000 ton (t) oligomerization product produced pert of oligomerization catalyst; and
    (b) adjusting the content of cyclopentene in the olefin-containing hydrocarbon feed to a level at or below 1.5 wt % based on the total weight of olefins in the hydrocarbon feed to maintain the deactivation rate.

2. The process of claim 1, wherein the olefin-containing hydrocarbon feed comprises an acyclic olefin selected from the group consisting of C$_3$, C$_4$, C$_5$ and C$_6$ olefins and mixtures thereof.

3. The process of claim 2, wherein the olefin-containing hydrocarbon feed comprises up to 50 wt % of butenes and up to 30 wt % of pentenes, based on the total weight of olefins in the olefin-containing hydrocarbon feed.

4. The process of claim 1, wherein the at least one acyclic olefin is selected from the group consisting of propene, butenes and pentenes.

5. The process of claim 1, wherein the oligomerization is carried out at a pressure in the range of from 500 psig to 1,500 psig and at a temperature in the range of from 130° C. to 320° C.

6. The process of claim 1, wherein the oligomerization catalyst is selected from the group consisting of zeolite and phosphoric acid-based catalysts.

7. The process of claim 1, wherein the oligomerization product has an initial boiling point (IBP) between 35° C. to 230° C. and a distillation range, dry point (DPT) between 72° C. to 260° C., wherein the IBP and DPT being determined in accordance with ASTM D86.

8. The process of claim 1, wherein the oligomerization product is subjected to hydrogenation to produce a hydrogenated oligomerization product.

9. The process of claim 1, wherein the oligomerization product is further processed by distillation and hydrogenation to obtain a hydrogenated oligomerization product.

10. The process of claim 9, wherein the hydrogenated oligomerization product
    has an initial boiling point (IBP) between 98° C. to 270° C. and a distillation range dry point (DPT) between 104° C. to 311° C., wherein the IBP and DPT being determined in accordance with ASTM D86.

11. The process of claim 1, wherein the content of cyclopentene in the olefin-containing hydrocarbon feed is adjusted by distillation or dilution of the olefin-containing hydrocarbon feed.

12. In a process for converting an olefin-containing hydrocarbon feed into an oligomerization product, wherein an olefin-containing hydrocarbon feed is contacted with an oligomerization catalyst in a reactor under conditions suitable to oligomerize the olefin to obtain a reactor effluent, the olefin-containing hydrocarbon feed comprising at least one $C_2$ to $C_{12}$ acyclic olefin and cyclopentene, the reactor effluent comprising an oligomerization product which comprises $C_6$ to $C_{16}$ cycloalkenes, the improvement comprising steps of:
- (a) selecting a desired content of $C_6$ to $C_{16}$ cycloalkenes in the oligomerization product;
- (b) adjusting a level of cyclopentene in the olefin-containing hydrocarbon feed to obtain the desired content of $C_6$ to $C_{16}$ cycloalkenes in the oligomerization product according to the following formula:

$A'$ (wt %)=0.25+1.93($B'$ (wt %))

wherein $A'$ is the level of cyclopentene in the olefin-containing hydrocarbon feed and $B'$ is the desired content of $C_6$ to $C_{16}$ cycloalkenes in the oligomerization product.

13. The process of claim 12, wherein the olefin-containing hydrocarbon feed comprises an acyclic olefin selected from the group consisting of $C_3$, $C_4$, $C_5$ and $C_6$ olefins and mixtures thereof.

14. The process of claim 13, wherein the olefin-containing hydrocarbon feed comprises up to 50 wt % of butenes and up to 30 wt % of pentenes, based on the total weight of olefins in the olefin-containing hydrocarbon feed.

15. The process of claim 12, wherein the at least one acyclic olefin is selected from the group consisting of propene, butenes and pentenes.

16. The process of claim 12, wherein the oligomerization is carried out at a pressure in the range of from 500 psig to 1,500 psig and at a temperature in the range of from 130° C. to 320° C.

17. The process of claim 12, wherein the oligomerization catalyst is selected from the group consisting of zeolite and phosphoric acid-based catalysts.

18. The process of claim 12, wherein the oligomerization product has an initial boiling point (IBP) between 35° C. to 230° C. and a distillation range, dry point (DPT) between 72° C. to 260° C., wherein the IBP and DPT being determined in accordance with ASTM D86.

19. The process of claim 12, wherein the oligomerization product is subjected to hydrogenation to produce a hydrogenated oligomerization product.

20. The process of claim 12, wherein the oligomerization product is further processed by distillation and hydrogenation to obtain a hydrogenated oligomerization product.

21. The process of claim 20, wherein the hydrogenated oligomerization product has an initial boiling point (IBP) between 98° C. to 270° C. and a distillation range dry point (DPT) between 104° C. to 311° C., wherein the IBP and DPT being determined in accordance with ASTM D86.

* * * * *